United States Patent [19]

Morrison et al.

[11] Patent Number: 5,066,830
[45] Date of Patent: Nov. 19, 1991

[54] PEPPER GAMETOCLONAL VARIATION

[75] Inventors: Robert A. Morrison; David A. Evans, both of Palmyra, N.J.

[73] Assignee: DNA Plant Technology Corporation, Cinnaminson, N.J.

[21] Appl. No.: 142,961

[22] Filed: Jan. 12, 1988

[51] Int. Cl.$^5$ .............................................. A01H 1/04
[52] U.S. Cl. ...................................... 800/230; 47/58; 435/240.51; 800/DIG. 40; 800/DIG. 41
[58] Field of Search .............................. 800/1; 47/58; 435/240.4, 240.51

[56] References Cited

PUBLICATIONS

Shifriss et al. (1971), Hortscience, vol. 7(1), Feb., p. 36.
Greenleaf, In. Bassett (1987) ed Breeding Vegetable Crops, the AVI Publishing Co. Inc., Westport, Conn.
R. A. Morrison (1987), Gametoclonal Variation in Pepper, Dissertation Abstracts International, vol. 48, No. 5, p. 1226-B.
Morrison, Gametoclonal Variation in Pepper, Ph.D. Dissertation submitted to Rutgers University, May 1987.
Morrison et al., J. Plant Physiol. 126: 1-9, 1986.
Vagera and Havreneh, Biol. Plant (Prague) 27: 10-21, 1985.
Johansson, Physiol. Plant 59: 397-403, 1983.
Bajaj, Handbook of Plant Cell Culture, vol. I, Chap. 6, D. A. Evans, W. R. Sharp, P. V. Ammilato, and Y. Yamada, eds., Macmillan, NY, 1983.
Johansson et al., Physiol. Plant 54: 24-30, 1982.
Sibi et al., Ann. Amelior. Plant 20: 583-606.
Charles et al., J. Hortic. Sci 54: 159-161, 1979.
Novak, F. Z. Planzeuzucht. 72: 46-54, 1974.
Wang et al., Sci. Sinisn. 165: 147-151, 1973.

*Primary Examiner*—Charels F. Warren
*Assistant Examiner*—Gary Benzion
*Attorney, Agent, or Firm*—Pennie & Edmonds

[57] ABSTRACT

The present invention relates to a method of recovering variants of species of the genus Capsicum by in vitro culture which comprises:

(a) culturing excised anthers on a first medium which promotes the initiation of embryos for a period of time and under conditions sufficient for initiation to occur;

(b) culturing initiated anthers in a second medium which promotes embryo development, the second medium comprising a first solid layer containing an effective amount of activated charcoal and a second aqueous layer containing no charcoal for a period of time and under conditions sufficient for embryo development to occur; and (c) recovering variant plantlets from embryos so produced.

17 Claims, No Drawings

PEPPER GAMETOCLONAL VARIATION

TABLE OF CONTENTS

1. Field of the Invention
2. Background of the Invention
3. Brief Description of the Invention
4. Detailed Description of the Invention
5. Examples
   - 5.1. Procedure for Producing Gametoclonal Variants
   - 5.2. Low-Seed Bell Gametoclone
   - 5.4. Regeneration of Interspecific Hybrid
   - 5.5. Intraspecific Hybrid Sorting

1. FIELD OF THE INVENTION

The present invention relates to a method of tissue culturing pepper plants. Specifically, the method relates to a method of anther culture of pepper plants useful in the regeneration of recalcitrant interspecific hybrids and inducing novel gametoclonal variants in pepper, as well as new varieties of peppers produced thereby.

2. BACKGROUND OF THE INVENTION

One of the primary goals of plant breeders is the continued production of improved crop plants. Because of the constant change in human needs and standards, there is a concurrent, constant need for the development of new plant varieties adapted to these changing standards. Nature itself does provide the raw materials upon which the necessary changes may be based, in the form of the frequent natural variation that is found to exist in many plant populations. Traditional plant breeding techniques have relied on the naturally occurring variation, combined with typical cross breeding of plant lines containing the desirable variations, to produce new varieties having the sought-after superior agronomic characteristics.

While this method has been routinely successful in producing large numbers of new plant varieties, the laborious procedures of crossing and backcrossing are timeconsuming and thus somewhat inefficient. Furthermore, not all plants exhibit a sufficient amount of natural variation or genetic combining ability to permit their routine use in plant breeding programs. Therefore, new methods for producing useful variants in a rapid, reliable manner are always being sought.

The tremendous advances made in plant cell and tissue culture in recent years have provided solutions to many of the problems inherent in traditional plant breeding programs. The ability to regenerate an entire plant from a single cell or a piece of plant tissue provides the possibility of propagating large numbers of presumably identical plants from a single parent plant having a desirable variation, thus avoiding the prolonged period to establish genetic uniformity necessarily involved in more typical breeding programs. The combination of the process of regeneration with a number of different methods of artificially inducing new variations permits the production of large populations of plants containing desirable variation. For example, the technique of protoplast fusion permits the combination of the nucleus of one plant type with the nucleus or cytoplasm of another plant type to provide a unique hybrid or cybrid, from which new plants may be regenerated by cell culture.

Somaclonal variation is another technique to which new varieties are commonly obtained. This method relies on the spontaneous occurrence of a small number of variants in the process of clonal propagation. These new variations often provide a convenient source for selection of new plant types which can then be regenerated in significant numbers by cell culture techniques.

Anther culture is also a potential source in the ultimate production of plant varieties. Anther culture involves the direct development of haploid embryos from pollen or microspores. Since $F_1$ hybrids may be heterozygous for several genes and recombination occurs during meiosis, the plants ultimately derived from pollen grains of $F_1$ hybrids often represent different homozygous genetic recombinants, thus again providing a convenient basis for selecting raw material for new varieties. Similarly, pollen derived plants are also known to express spontaneous variations, much like those observed in plants cultured from somatic tissue. This phenomenon in pollen-derived plants is known as gametoclonal variation. Haploid breeding, in addition to providing avenues of obtaining new variants, may also reduce the time required to establish new varieties by several generations.

Although all the aforementioned in vitro techniques have contributed significantly to the recent advances in cell culture plant breeding, one of the problems inherent in their use is that the conditions required to ultimately achieve the successful production of new plants by any of these methods are almost always species- or at best genus-specific. This means that the culturing conditions which successfully yield new plants in one plant type cannot be reliably expected to operate successfully in even another closely related species. Thus, for each different species, new techniques must be developed, or else a trial-and-error procedure of modification of known techniques must be gone through in order to achieve the appropriate combination of conditions. Further, even when a successful technique is discovered for a particular species, it is frequently the case that an interspecific hybrid involving the same species will not be amenable to that technique. Thus, any known methods are assumed to be highly limited with respect to the breadth of their potential utility. Finally, although many techniques may be successful in yielding new plantlets, if the numbers of plants produced is not high, the practical utility of the method in a crop improvement program is very limited.

In connection with the present invention, however, a method of anther culture was developed with respect to the pepper, Capsicum which has been found to have a broad spectrum of applicability to production of embryos of different pepper strains. Although anther culturing of peppers has been previously described in the scientific literature (see, for example, Wang et al., *Sci. Sinica*, 16S:147-151, 1973), many reported techniques have not been able to produce an adequate number of plants. Subsequent work (Sibi, et al., *Ann. Amerlior. Plant* 20:583-606, 1979), while increasing the numbers of regenerable plants, has not produced a technique which is successful in allowing regeneration of $F_1$ interspecific hybrids from pollen, nor have gametoclonal variants been reported from known techniques. The present method of anther cultures, however, not only reliably produces large numbers of embryos of a number of individual strains of pepper, but also, surprisingly, is effective in producing embryos from pollen of interspecific hybrids as well as reliably producing gametoclonal variants.

3. BRIEF DESCRIPTION OF THE INVENTION

The present invention relates to a method of recovering variants of species of the genus Capsicum by in vitro culture which comprises:

(a) culturing excised anthers on a first medium which promotes the initiation of embryos for a period of time and under conditions sufficient for initiation to occur;

(b) culturing initiated anthers in a second medium which promotes embryo development, the second medium comprising a first solid layer containing an effective amount of activated charcoal and a second aqueous layer containing no charcoal for a period of time and under conditions sufficient for embryo development to occur; and (c) recovering variant embryos so produced.

The present invention also relates to low-seed bell peppers, having from 0 to about 20 seeds, as well as mutants, clones, somaclones, gametoclones, and hybrid derivatives thereof, which retain the low-seed trait. By "hybrid derivatives" in the present context is meant the low-seed progeny produced by traditional cross-breeding or protoplast fusion of the low seed bell with other varieties.

As employed herein the phrase "initiation of embryos" means stimulation of pollen to divide repeatedly and normally, without a tendency to abort; the phrase "embryo development" means further growth of the initiated embryos in a manner which will lead to plantlet development.

4. DETAILED DESCRIPTION OF THE INVENTION

The process of the present invention not only is capable of stimulating regeneration of pepper anthers in large numbers than have previously been obtainable, but it also has provided the means by which recalcitrant combinations such as interspecific $F_1$ hybrids and other species of Capsicum can be routinely regenerated, a feat which has not heretofore been accomplished. The fundamental steps of the invention involve initiation of embryo development on a solid medium followed by transfer of the initiated anthers to a second medium containing activated charcoal to promote further embryo development and differentiation.

The procedures and principles involved in anther culture are well known in the art and are discussed generally in Evans, et al., *Handbook of Plant Cell Culture*, Vol. I, Chap. 6, 1983. Generally speaking, pollen at the uninucleate stage, just before the first mitosis or during mitosis are most readily stimulated for induction of androgenesis. In the case of peppers, an estimate of the proper timing can be made by harvesting flower buds when the corolla is slightly higher than the calyx. The state of microspores within anthers may be accurately determined by staining of anther squashes in acetocarmine stain. Anthers containing microspores at the late uninucleate stage of development were chosen for culture. Cold treatment is frequently used as a method of increasing the frequency of androgenesis; the typical treatment is exposure to temperatures of about 4° C. for a period of about 40–120 hours, with 100 hours appearing to be an optimal length of exposure. It should be noted, however, that the cold treatment does not initiate androgenesis, but simply enhances the viability of cultured pollen and represses differentiation; therefore, since the result of the treatment is indirect, it is not a prerequisite for culture. More important, however, is the use of a pretreatment at elevated temperatures, generally about 30° C. Failure to utilize this heat pretreatment will result in reduced numbers of initiated anthers. The preferred length of heat exposure is generally about 6–10 days at 35° C. The flower buds are preferably surface-sterilized with a disinfectant such as dilute sodium hypochlorite or ethanol, prior to the first culture step.

A variety of different culture media have been used to stimulate the induction of androgenesis in peppers (See, for example, Novak, F., *Z. Planzezucht.* 72:46–54, 1974; Sibi, et al., *Ann. Amelior. Plant* 29:583–606, 1979; Vagera and Havranek, *Biol. Plant* (Prague) 27:10–21, 1985). In the present method, virtually any medium which will stimulate and promote embryo initiation and development is suitable for use. The preferred medium composition is a combination of C medium, for original initiation of embryos, and R medium, for final embryo development and differentiation; these media have been described in Sibi, *et al., supra*. While these media form the basic substrate, they may be modified to some extent by the addition of certain supplements such as growth hormones. The C medium, which is solid, is most advantageously supplemented with a small amount, generally no more than about $10^{-8}$M, of an auxin or combination of auxins. The preferred auxin is 2,4-Dichlorophenoxyacetic acid (2,4-D). This medium also benefits by the addition of between 5–10% sucrose, preferably about 6%. R medium is preferably prepared without the addition of hormones but may be supplemented with a small amount, usually between 1–5%, sucrose as well.

The most critical modification to the R medium, however, is the addition of activated charcoal and the preparation of a double layer. The use of activated charcoal has been described by Johansson, *Physiol. Plant* 54:24–30, 1892 and *Physiol. Plant* 59:397–403, 1983 but has only been demonstrated as being operative with certain species, using other media, and has never been employed with pepper. Further, it has not been shown to be capable of inducing the development of interspecific hybrid embryos. Nor has it been implicated in inducing gametoclonal variation. As noted above, this particular feature is critical to the success in the development of embryos from recalcitrant genotypes. The charcoal-containing step must be performed as a double layer, i.e., one layer of solid medium overlaid with a second layer of aqueous medium. The solid medium should contain between 1–5% activated charcoal and preferably contains about 2% charcoal. The presence of charcoal in the solid medium above is not sufficient to achieve the desired result; however, the solid layer must be covered with an aqueous layer of the same medium, the aqueous medium being prepared without added charcoal.

With the use of C medium, the anthers are placed upon the medium and incubated in the dark for a period of 6–10 days at temperatures of about 30°–40° C., preferably above about 35° C. The anthers on Medium C are then transferred to 25° C., again in the dark, for an additional 2–6 days. This period of time on Medium C is generally sufficient to stimulate the initiation of androgenesis. Following the culture period on Medium C, the initiated anthers are transferred to a double-layered R medium; the lower solid layer contains activated charcoal and is overlaid with a liquid layer of R medium without added charcoal. The anthers are floated on the liquid medium and are left in this condition until embryos begin to appear. The usual period of time required for production of embryos is 2–4 weeks. When embryos begin to appear, they may be transferred to fresh medium R where plantlet development usually occurs within 2–3 weeks. Plantlets may then be transferred to soil. Plantlets may be tested for ploidy by any routine technique. Generally, both haploid and diploid plantlets are derived from the embryos. The diploid plantlets, in almost all cases, are of microspore origin and represent a spontaneous doubling of the originally haploid microspore; this has been verified by electrophoretic demonstration of homozygosity. Haploid plants, on the other hand, will normally have to be doubled. It is possible to induce chromosome duplication in a number of ways. For example, sold or heat shocks often lead to a doubling of chromosomes. Also, a number of chemical agents such as acenapthene, chloral hydrate, ethyl mercury chloride, 8-hydroxyquinoline and sulfanilamide are also known to be capable of inducing polyploidy. By far, the chemical agent of choice, however, is the drug colchicine because of its water solubility and reliability in producing high proportions of polyploid cells in treated plants. Generally, the colchicine is added, in a lanolin paste, to the haploid plant by application to the axils of the plant leaves. Diploid plants can be verified by chromosome number, guard cell counts, or morphology.

As noted above, the use of R and C media in the present method is preferred, but it is also possible to employ the present methods with virtually any culture medium or combinations of media which will stimulate embryo growth and development in Capsicum. The present method is applicable to the production of embryos from anthers of any variety of the genus Capsicum and any interspecific or intraspecific hybrid of that genus. As used in the present specification and claims, the phrase "recovery of variants" is intended to encompass the variants produced routinely as a result of gametoclonal variation as well as the recovery of recombinant variants resulting from meiotic events in pollen production; this is especially useful in application to regenerate inter-specific or intraspecific hybrids from anther culture.

The present method has given rise to a substantial number of gametoclonal variants having unusual characteristics. One variant in particular has been isolated which displays an extremely valuable consumer characteristic: anther culture of a yellow-fruited bell produced one variant having an abnormally low seed count. In plant lines derived from this variant, there is some variation within each plant as to the number of seeds per fruit, but the maximum number of seeds is typically 20, with the range running from 0–20 seeds. When this line was grown in the field, rarely are there no seeds, but when greenhouse grown, completely seedless fruit is more common.

Crosses using this low seed variant line as female parent present difficulty because of the low frequency of seed set; similarly selfing the plant is also difficult, but not impossible. However, crosses using a low seed doubled haploid as pollen parent are easily made. Typically, crosses between the low seed variant and other varieties of pepper yield $F_1$ hybrids containing seed amounts which are normal when compared with similar $F_1$ hybrids using the original yellow pepper cultivar, from which the variant was obtained as a parent. However, the $F_2$ generation of the hybrid with the low seed parent yielded normal seed and low seed lines in a ratio of approximately 3:1. Thus, it is possible to routinely recover low-seeded progeny from $F_2$ generation hybrids through traditional breeding methods as well as to produce additional low-seeded plants by cloning the low seed lines.

5. EXAMPLES

5.1. PROCEDURE FOR PRODUCING GAMETOCLONAL VARIANTS

This example describes the double layer protocol from which gametoclonal variants have been produced:

C and R medium was prepared in accordance with the compositions described in Sibi, et al. Ann. Amelior. Plants 20(5):583–606 (1979) with the exception that 2% activated charcoal was supplemented to the C medium:

| Elements, in mg/liter of medium | Medium C | Medium R |
| --- | --- | --- |
| $KNO_3$ | 2150 | 2150 |
| $NH_4NO_3$ | 1238 | 1238 |
| $MgSO_4\ 7\ H_2O$ | 444 | 444 |
| $CaCl_2\ 2\ H_2O$ | 313 | 313 |
| $KH_2PO_4$ | 142 | 142 |
| $Ca(NO_3)_2\ 4\ H_2O$ | 50 | 50 |
| $NaH_2PO_4\ H_2O$ | 38 | 38 |
| $(NH_4)_2SO_4$ | 34 | 34 |
| $KCl$ | 7 | 7 |
| $MnSO_4\ H_2O$ | 22.130 | 20.130 |
| $ZnSO_4\ 7\ H_2O$ | 3.625 | 3.225 |
| $H_3BO_3$ | 3.150 | 1.550 |
| $KI$ | 0.695 | 0.330 |
| $Na_2MoO_4\ 2\ H_2O$ | 0.188 | 0.138 |
| $CuSO_4\ 5\ H_2O$ | 0.016 | 0.011 |
| $CoCl_2\ 6\ H_2O$ | 0.016 | 0.011 |
| Mesoinositol | 50.300 | 50.300 |
| Pyridoxine (HCl) | 5.500 | 5.500 |
| Nicotinic acid | 0.700 | 0.700 |
| Thiamine (HCl) | 0.600 | 0.600 |
| Calcium pantothenate | 0.500 | 0.500 |
| Biotin | 0.005 | 0.005 |
| Glycine | 0.500 | 0.500 |
| $Na_2E.D.T.A.$ | | |
| $FeSO_4\ 7\ H_2O$ | 13.90 | 13.90 |
| Sucrose | 6% | 3% |
| Sea plaque agarose (FMC Corp.) | 1.0% | 1.0% |
| 2,4-D | $10^{-8}$ M | — |
| pH | 5.7 | 5.7 |

R medium to be used as the second liquid layer does not contain agarose and is not supplemented with 2% activated charcoal.

Flower buds are harvested from a number of different plant varieties when the corolla was slightly higher than the calyx. The state of the microspores within the anthers was determined by staining anther squashes in aceto-carmine stain, and anthers containing microspores at the late uninucleated stage of development were selected. Flower buds were treated at a temperature of about 4° C. for a period of about 100 hours.

Pretreated flower buds were surface sterilized in 20% commercial clorox (1.5% sodium hypochlorite) for 15 minutes followed by three rinses in sterile distilled water. Anthers were dissected and cultured on Medium C. Anthers were randomly sampled after culture to estimate the amount of anthers with late uninucleate microspores. Cultures were incubated at 35° C. in the dark for eight days (Dumas DeVaulx, et al., 1982). After eight days, anthers on Medium C were transferred to 25° C. in the dark for an additional 4 days. After a total of twelve days on Medium C, anthers were transferred to the double layer charcoal medium. After transfer from Medium C, embryos appeared in the pollen sacs of cultured anthers in 2–4 weeks. Embryos, when transferred to fresh Medium R, developed into plantlets in an additional 2-3 weeks. Plantlets with sufficient root development were transferred to soil under high humidity and were acclimated from culture environment to that of a greenhouse by gradually reducing the humidity. Plants were verified as haploid or diploid by cytological examination of specially prepared meristematic tissue by counting the number of chromosomes (12=haploid; 24=diploid). Alternatively, the number of chloroplasts within stomata of leaf epidermis can be used to distinguish haploid from diploid plants (haploid plants have essentially half the number of chloroplasts as a diploid plant ranges of diploid being between 13-20, and ranges of haploid being between 5-10). Once the ploidy of the plants has been established, the chromosome number of the haploid plants must be doubled in order to restore fertility for subsequent seed collection. Diploid plants did not require treatment.

As doubled haploids are completely homozygous, variation (gametoclonal) is observed directly in the $R_o$ generation. Analysis of selfed progeny for the purpose of observing recessive traits is not necessary; however, progeny evaluation is necessary to distinguish genetic from epigenetic changes. Observation of variation among the progeny indicates that the change is genetic. Progeny evaluation of gametoclonal variants is accomplished by selfing $R_o$ plants and evaluating the progeny (now a line) in the field by comparing to progeny derived by selfing donor plants originally used to obtain anthers from which the gametoclones were produced. As the gametoclone line is true-breeding, pure seed can be obtained by selfing any plant in the line.

Utilizing the foregoing procedures a number of different gametoclonal variants were obtained in several varieties of C. annuum. Among these are: a variant of "Calwonder" (2—2) which has upward oriented fruit; a dwarf variant (7-10) of the commercial $F_1$ hybrid "Stokes Early Hybrid"; an "Emerald Giant" variant characterized by extreme reduction in fruit width; and a variant of a yellow-fruited "Calwonder" bell pepper variety, having strongly reduced seed amount. A bell pepper is generally understood in the trade to designate a pepper having approximately equal dimensions of length and width, resulting in a "block" shape; the fruit is also multilobed, i.e., possessing 3 or more lobes. The aforementioned low-seeded bell has been used to establish a bell, low-seeded line, designated as "Bell-sweet," by tissue culture of the original gametoclonal variant. The low seed trait has proven stable over several generations. The low seed bell has also been employed in a traditional breeding program with other varieties to produce a number of low seed, hybrid variants. Among these is a new low-seed, small, very sweet and brightly colored variant, designated as "Vegi-Sweet", has also been isolated. The details of the production of both the cloned and cross bred low seed lines are presented in Examples 2 and 3.

5.2. LOW-SEED BELL GAMETOCLONE

The details of the tissue culture have been discussed above, utilizing the C and R media as previously defined in Example 1. Among the gametoclones obtained in the process was a low-seed bell pepper, generally having from 0-20 seeds. This has been designated as line 9-1 and given the name Bell-Sweet.

The progeny of the original low-seed bell gametoclone have consistently been all low-seed. Further, the selfing of these progeny has also yielded only low-seed plants, thus showing the stability of the trait. Table 1 below shows the results of the selfing as well as the results of crosses with a normal bell (P.I. 368140) and the results of selfing the progeny of that cross.

TABLE 1

|  | Normal | Low Seed | $X^2$ |
|---|---|---|---|
| 9-1 × self | 0 | 30 | — |
| 9-1 × P.I. 368140 | 30 | 0 | — |
| (9-1 × P.I. 368140)x | 82 | 20 | 1.581 |

Other characteristics of Bell-Sweet include a fruit shape and size similar to cultivars such as Calwonder or Emerald Giant. The plant height is generally around 60.0 cm yield, about 20 fruit per plant. The average fruit width is about 8.4 cm, length about 7.0 cm, with a wall thickness of about 0.5 cm.

Comparisons of the low seed bell pepper with a normal bell pepper, under identical growing conditions in several locations, show a significant difference in seed number, as outlined in Table 2.

TABLE 2

| VARIETY | LOCATION | MEAN |
|---|---|---|
| 9-1 | Puerto Rico, 1987 | 8.9[a] |
| Yolo Wonder | Puerto Rico, 1987 | 329.05[a] |
| 9-1 | San Marcos, 1987 | 8.74[b] |
| Yolo Wonder | San Marcos, 1987 | 328.8[b] |
| 9-1 | Rancocas, 1987 | 9.4[c] |
| Yolo Wonder | Rancocas, 1987 | 335.34[c] |

[a] $p < 0.01$
[b] $p < 0.01$
[c] $p < 0.01$

Seedless peppers are known to occur naturally, as a result of parthenocarpy, or the growth of fruit without fertilization. The parthenocarpy can in fact be induced, under low temperature conditions, by the application of growth regulators, and may also occur occasionally in unpollinated flowers of genetically male sterile plants. However, seedless fruits produced by any means usually is deformed in some manner, either by virtue of the environmental conditions which provoke it, or by the physical absence of seeds per se. Therefore, pepper plants which regularly produce normal, low-seeded fruit under normal pepper growing conditions have not heretofore been known. The present invention thus provides a means by which pepper plants with essentially all low seed fruits with normal morphology can be predictably produced by traditional breeding methods. The method of gametoclonal variation has provided a low-seed gametoclone, Bell-Sweet, which has proven stable over several generations. However, not only can the technique itself be used to produce low-seed variants; the present low-seed bell has been used as a parent in numerous crosses with normal pepper lines to produce low-seed hybrid peppers of other types by traditional breeding methods. The small, low-seed pepper known as Vegi-Sweet, described in Example 3, was obtained by this method. The fruit of all low-seed plants produced by this method has always been substantially identical in size and shape to normal, seeded fruit of the parental variety. In this manner they can be distinguished from seedless fruit produced by parthenocarpy. The low seed fruit of the present invention can also be used as source material for development of low seed variants by gametoclonal variation, somaclonal variation and mutagenesis. The seed of this pepper have been deposited with the National Seed Storage Laboratory, under accession number NSSL 214,296.

5.3 LOW-SEED SWEET JALAPENO-TYPE PEPPER

The pepper variety Vegi-Sweet is a small-fruited sweet pepper developed for the snack vegetable market. It is an open-pollinated variety derived from pedigree selection of a cross between the bell pepper variety Bell-Sweet (described in Example 2) and a small-fruited breeding line U.S.D.A. P.I. 379183. The strategy was to combine the flavor, texture, and low-seed characteristic of Bell-Sweet with the small fruit size of P.I. 379183. The $F_1$ hybrid was characterized by long thin, red fruits containing an average of 300 seeds. The hybrid was selfed in the greenhouse, and 300 $F_2$ plants were grown in seedling trays and allowed to produce a single fruit. All plants exhibiting a noticeable reduction in seed amount were self-pollinated in preparation for field evaluation. Among the 300 $F_2$ plants screened for seed amount, 60 were low seed. Of the 60 plants 15 were considered as adequate regarding fruit size and shape and advanced as $F_3$ lines to the field for evaluation.

Evaluation of these lines in the field at San Marcos, California resulted in the identification of one line that was suitable for flavor and seed amount. Three other lines were selected for yield and seed amount. The best line has been designated VS-1.

Segregation occurred for subtle changes in fruit shape and size. All plants in the line exhibited fruits with a dark green immature color that ripened to deep red. Fruits from all plants in the line had few or no seeds. The fruit shape that predominated was that of a jalapeno. Fruits were smooth and uniform with no distortion.

Plant type is mostly compact with only a few plants that exhibited elongated internodes. Foliage cover was similar to that of Bell-Sweet. Segregation was observed for peduncle orientation (bent and straight) with many of the smaller fruited plants having upright fruit.

Immature green fruit have the flavor of a green bell and not the off-flavor of the P.I. 379183 parent. In contrast to jalapeno, the walls of Vegi-Sweet (VS-1) are thinner and the fruits are more flat than they are round. The skin is thick and persistent which adds more crunch when the fruits are bitten. The seed of this pepper have been deposited with the American Type Culture Collection under accession number ATCC 40411.

5.4. REGENERATION OF INTERSPECIFIC HYBRID

An attempt was made to produce haploid plants from an interspecific $F_1$ hybrid between the *C. annuum* variety "Emerald Giant" and *C. chinense* (CA4). It had been determined previously that anther culture of "Emerald Giant" alone on the C and R medium without the use of the double layer method was routinely capable of producing large numbers of embryos. However, when the same technique was used to initiate embryo development, in the interspecific hybrid of *C. chinense* and *C. annuum*, no embryos were produced.

Anther culture utilizing the double layer method described in Example 1 was then tried with the interspecific hybrid. The results shown in Table 1 indicate that the double layer method is capable of inducing embryo development from interspecific hybrids which cannot be anther-cultured by known methods.

TABLE 3

| Genotype | Culture Method | Another Cultured | Embryos |
|---|---|---|---|
| Emerald Giant | R* | 15 | 14 |
| E.G. × CA4 | R | 200 | 0 |
| Emerald Giant | D.L.+ | 15 | 100+ |
| E.G. x. CA 4 | D.L. | 25 | 100+ |

*C and R medium without charcoal
+Double-layer charcoal medium

5.5 INTRASPECIFIC HYBRID SORTING

The anther culture method described herein has been used to accomplish hybrid sorting of an intraspecific $F_1$ hybrid. Intraspecific hybrid sorting has been successfully utilized to transfer high solids traits from one processing pepper variety to another. A variety designated D2 is a widely-grown processing bell pepper variety with good yield and intense dark-green fruits. The variety Yolo Wonder is also widely grown because it has high total solids. Hybrids between these cultivars were constructed and used to obtain anthers for subsequent anther culture according to the procedure described herein. Resulting DHs were raised to maturity, self-pollinated, and seeds were subsequently collected. Seeds, representing progeny of regenerated DH plants, were sown in the field at two locations in the Modesto, California area during the summer of 1987. Replicated DH lines were evaluated for fruit color, yield, and total solids. A total of 85 DH lines were evaluated; 44 lines were designated as having dark-green fruit (that of the D2 parent) and 41 had light-green fruit similar to the Yolo Wonder B parent. The inheritance of this trait has been described previously to be conferred by two loci indicating that four phenotypic classes would be expected. Among the DH lines there appeared to be a spectrum of fruit color from dark to intermediate to light indicating the occurrence of these classes. The designation of fruit color as light or dark provided a simplification to demonstrate a gametic array for this trait.

All DH lines were analyzed for total solids. This characteristic is determined by the percentage of dry weight measured in the fruit wall (meat) tissue which was separated from the placenta core and septum tissues. Total solids values ranged from 5.0 to 7.0%. Control lines of D2 had a mean total solids of 5.9 while Yolo Wonder B control lines had a mean total solids of 6.22%. This finding indicated that a gametic array was achieved for total solids. Lower and higher solids observed among the DH Lines compared to controls indicated that trangressive segregation had occurred for this multigenic characteristic.

Evaluation of the high solids lines for yield indicated that eleven lines exhibiting high solids also had a yield that was equivalent or better than the D2 control lines. Of these lines, one also had dark-green fruit. This result indicates the successful application of hybrid sorting to transfer high solids genes of Yolo Wonder B into D2.

Solids data from this line is presented along with that of the controls in Table 4.

TABLE 4

| | SOLIDS | |
|---|---|---|
| LINE | LOCATION 1 | LOCATION 2 |
| DH 3 | $6.22^a$ | $6.52^b$ |
| D2 | $5.67^a$ | $5.70^b$ |

TABLE 4-continued

| LINE | SOLIDS | |
| --- | --- | --- |
| | LOCATION 1 | LOCATION 2 |
| Yolo Wonder | 6.12 | 6.32 |

*p <0.01
bp <0.01

What is claimed is:

1. A plant of the pepper species capsicum annuum which regularly produces low-seed fruit having 0 to about 20 seeds, which plant possesses neither a male sterile nor female sterile trait and which low seed trait is not a result of environmental or chemical induction.

2. The plant of claim 1 which produces bell-type peppers.

3. The plant of claim 2 which produces sweet jalapeno-type peppers.

4. the plant of claim 2 which is produced by seed having the accession number NSSL 214,296, mutants, clones, somaclonal variants, gametoclonal variants and hybrid derivatives thereof in which the mutants, clones, somaclonal variants, gametoclonal variants, and hybrid derivatives retain the low seed trait.

5. The plant of claim 3 which is produced by seed having the accession number ATCC 40411, mutants, clones, somaclonal variants, gametoclonal variants, and hybrid derivatives thereof in which the mutants, clones, somaclonal variants, gametoclonal variants, and hybrid derivatives retain the low seed trait.

6. A low seed fruit produced by capsicum annuum plant which regularly produces fruit having 0 to about 20 seeds, which plant possesses neither a male sterile nor female sterile trait, and which low seed trait is not produced by environmental or chemical induction.

7. The fruit of claim 6 which is a bell-type pepper.

8. The fruit of claim 6 which is a sweet jalapeno-type pepper.

9. A seed of the fruit of claim 6.

10. A seed of the fruit of claim 7.

11. A seed of the fruit of claim 8.

12. A pepper seed having the accession number NSSL 214,296.

13. A pepper seed having the accession number ATCC 40411.

14. A plant produced by the seed of claim 12.

15. A plant produced by the seed of claim 13.

16. A fruit produced by the plant of claim 14.

17. A fruit produced by the plant of claim 15.

* * * * *